(12) United States Patent
Abraham

(10) Patent No.: US 11,786,164 B2
(45) Date of Patent: Oct. 17, 2023

(54) OLFACTORY-ACTION METER FOR PRECISE QUANTIFICATION OF OLFACTORY DYSFUNCTIONS AND NEUROCOGNITIVE DEFICITS

(71) Applicant: Indian Institute of Science Education and Research, Pashan (IN)

(72) Inventor: Nixon Mundathukudiyil Abraham, Pashan (IN)

( * ) Notice: Subject to any disclaimer, the term of this patent is extended or adjusted under 35 U.S.C. 154(b) by 78 days.

(21) Appl. No.: 17/443,527

(22) Filed: Jul. 27, 2021

(65) Prior Publication Data
US 2022/0054075 A1 Feb. 24, 2022

(51) Int. Cl.
*A61B 5/00* (2006.01)
*G01N 33/00* (2006.01)

(52) U.S. Cl.
CPC ........ *A61B 5/4011* (2013.01); *G01N 33/0001* (2013.01)

(58) Field of Classification Search
CPC ..... A61B 5/4011; A61B 5/00; G01N 33/0001
See application file for complete search history.

(56) References Cited

U.S. PATENT DOCUMENTS

| 9,936,913 | B2 * | 4/2018 | Mills | A61M 15/08 |
|---|---|---|---|---|
| 2007/0113854 | A1 * | 5/2007 | Mcauliffe | A61M 16/1055 |
| | | | | 128/205.27 |
| 2010/0018535 | A1 * | 1/2010 | Chimenti | A61M 16/06 |
| | | | | 128/206.24 |
| 2014/0069428 | A1 * | 3/2014 | Sears | F16K 5/0407 |
| | | | | 128/204.21 |
| 2019/0200910 | A1 * | 7/2019 | Lee | G16H 50/20 |
| 2020/0072859 | A1 * | 3/2020 | Takagi | G01N 35/04 |
| 2020/0253531 | A1 * | 8/2020 | Smith | A61B 5/4088 |

* cited by examiner

*Primary Examiner* — Eric F Winakur
*Assistant Examiner* — Emily C Clement
(74) *Attorney, Agent, or Firm* — Gearhart Law, LLC; David Postolski

(57) ABSTRACT

The present disclosure relates to an apparatus (100) for quantitative assessment of olfactory dysfunctions and neurocognitive deficits, the apparatus includes first filters (104-1) adapted to sterilize air received from an air pump, a second filter (106) filter odor molecules from the air, a manifold (108) adapted to split the sterilized air into a plurality of channels, at least one channel carries the sterilized air to a first MFC (110) and adjacent channels carry sterilized air to second MFCs (112). Each container in a reservoir (114) filled with an odorant different from adjacent containers, and a nozzle (118) adapted to receive the odorized air from the reservoir that is inhaled by a subject through an odor delivery unit (124), based on degree of variation in volumetric concentration of the odorants, quantitative assessment of olfactory dysfunction is determined.

9 Claims, 8 Drawing Sheets

OLFACTORY-ACTION METER FOR PRECISE QUANTIFICATION OF OLFACTORY DYSFUNCTIONS AND NEUROCOGNITIVE DEFICITS

CROSS REFERENCE TO RELATED APPLICATION

This application is a Non-Provisional Utility application, which claims a priority to 202021035482 filed in India on Aug. 18, 2020, the disclosures of which is incorporated its entirety by reference herein.

TECHNICAL FIELD

The present disclosure relates, in general, to an apparatus for determining olfactory dysfunction, and more specifically, relates to highly sensitive and precise olfactory-action meter apparatus and a method to assess whether a person is suffering from olfactory dysfunction and cognitive deficits.

BACKGROUND

Olfactory dysfunction is a condition in which a person loses/has reduction in his/her ability to smell. The occurrence of this condition may be early signs of several underlying conditions such as aging, sinus disease, respiratory tract infection or even neurological disorder. Hence, the test to determine olfactory dysfunction is crucial in assessing the underlying medical condition of an individual.

Currently, a novel coronavirus, named COVID-19, has been threatening the global community to such a level that the spread of the COVID-19 has turned into a pandemic. At the moment, it is entirely known how and why the spread of the virus occurs. One of the reasons for its unpredictable nature is a large fraction of infected people are asymptomatic, yet are carriers that effectively transmit the disease. Finding and isolating these silent carriers is a critical step to prevent the spread of disease. Sudden loss of olfaction (anosmia) has been self-reported by COVID-19 patients from different countries.

Recently, the researchers have understood the mechanism behind the loss of olfaction in COVID-19 patients. The novel coronavirus, also known as severe acute respiratory syndrome coronavirus 2 (SARS-CoV-2), enters the host cell by binding angiotensin-converting enzyme-2 (ACE2) receptors, followed by priming of the viral spike protein by the Transmembrane serine protease (TMPRSS2). These receptors are expressed in the non-neuronal supporting cells in the olfactory epithelium, but not in olfactory sensory neurons. Therefore, it is possible to have a gradual loss of sense of smell in patients. To quantify olfactory deficits of varying severity, we need to develop sensitive methods with utmost precision.

There have been several attempts to provide improvements to the existing olfactometers by providing various solutions for changing the concentration of the dilution flow, using a plurality of odorants. However, many of these devices do not produce reliable results, and this has limited the effectiveness of these instruments in terms of sensitivity, accuracy, speed, precision and of the results reproduced.

Some of the patents that disclose olfactory devices are cited herein. However, no instruments/devices reported yet for quantifying olfactory deficits in patients with contagious infectious diseases. An existing olfactometer comprising a plurality of bottles connected to independent distribution flow channels defined in a distribution block, and separate tubing connecting to each of the independent distribution flow channels to an outlet piece, wherein a consistent amount of gas stimulus contained within one of the bottles is selectively discharged through the outlet piece using at least one actuator for inhalation by a test subject. The bottles can be easily and quickly removed from the distribution block and easily interchanged for rapid testing of different gas stimuli, while eliminating cross-contamination through the use of the independent flow channels and separate replaceable tubing. The olfactometer may also include a computing device that selectively operates the at least one actuator to coordinate the release of the gas stimulus from one of the bottles and the inhalation of the gas stimulus by the test subject in conjunction with a visual and/or audio cue.

Another existing device comprises (i) a source of carrier gas flow; (ii) regulating means which receives the carrier gas flow and regulates its passage through a plurality of channels; (iii) downstream of the regulating means a plurality of aroma substance containing cartridges, one being associated with each channel, and (iv) disseminating means located in close proximity to the cartridges and adapted to deliver the individual aroma substances from the cartridges to nasal cavities by means of a conduit. The regulating means is any commercially available device, typically a device that comprises a plurality of channels adapted to convey the gas to cartridges containing aroma substance, one cartridge per channel. Thus, by opening and closing channels and maintaining these openings and closings for predetermined times, the regulating means can determine which aroma substances and how much thereof are conveyed and thus alter the nature of the aroma perceived by a user.

Yet another existing research article proposes an olfactometer device capable of delivering an unlimited number of odorants with temporal precision and no detectable inter-trial or inter-channel contamination. The olfactometer includes two main components: 1) a delivery arm, which directs odorant delivery to the experimental preparation, and 2) a flow control housing, containing airflow controls. Mean concentration of odorant delivery may be instantaneously modulated by varying channel pressure. However, the above mentioned existing devices do not quantify olfactory deficits in patients with contagious infectious diseases.

The nasal entry route of SARS CoV-2 to the central nervous system and the expression of molecular factors contribute to the neurological impairments of varying severity. However, the extent to which different variants of SARS CoV-2 can cause long-term maladaptive changes to the brain functionality is not well understood. This is partly due to the lack of precise non-invasive methods to track the infected individuals for longer time post the infection. While accurate behavioral readouts reflecting cognitive abilities could enable long-term tracking of neurological impairments, sensitive quantitative method(s) are scarce.

While an olfactory function test could facilitate the identification of asymptomatic carriers, precise quantitative characterization of the extent of olfactory loss in such individuals cannot be determined. Therefore, there is a need in the art to provide a high sensitivity, with utmost precision and yet simple to operate instrument that can conduct quantitative olfactory function test to assess loss of olfaction in individuals by solving the aforementioned problems.

Objects of the Present Disclosure

An object of the present disclosure relates, in general, to an apparatus for determining olfactory dysfunction, and more specifically, relates to highly sensitive and precise olfactory-action meter apparatus and a method to assess whether a person is suffering from olfactory dysfunction and cognitive deficits.

Another object of the present disclosure provides an apparatus, which is sensitive, rapid, low-cost, and achieves high-throughput screening of olfactory fitness and cognitive deficits.

Another object of the present disclosure provides an apparatus that provides separate optimized paradigms to pick up sensory and cognitive deficits.

Another object of the present disclosure provides an apparatus that enables real-time update of the performance.

Another object of the present disclosure provides an apparatus that provides a readout of mass flow controllers, which allows the operator to monitor the flow rates in real-time and modify if needed.

Another object of the present disclosure requires minimum training to operate the apparatus and can be handled easily.

Another object of the present disclosure provides the use of different types of odors which can be extrapolated to identification task if socially relevant odors are used.

Another object of the present disclosure provides an apparatus that delivers each odor using a separate channel, hence mixing of the odors can be prevented.

Another object of the present disclosure provides an apparatus that enables independent control of the mass flow controllers that allows odors to be delivered in different combinations. As ten independent odor lines are present, many mixtures of varying complexity can be generated.

Another object of the present disclosure provides the advantage of getting verbal readouts from patients with infectious diseases and recording a motor action by pressing the button of a response boxin case of non-infectious diseases.

Another object of the present disclosure provides a layout of the response box, where use of repeat button if the subjects are not able to sample either of the odors in odor matching paradigm.

Another object of the present disclosure can customize the paradigm to the needs of clinical requirements to probe different olfactory abilities. The variable parameters are a duration of odor pulse, inter-stimulus interval and inter-trial interval. This allows to get the readout of working memory.

Yet another object of the present disclosure provides an apparatus in which depending on the needs, a screen can be placed in front of the subject, which can give a visual indication of the delivery of odors and response timers. This allows to record the reaction times shown by subjects, which is crucial for patients with Parkinson's disease.

SUMMARY

The present disclosure relates, in general, to an apparatus for determining olfactory dysfunction, and more specifically, relates to highly sensitive and precise olfactory-action meter apparatus and a method to assess whether a person is suffering from olfactory dysfunctions and/or cognitive deficits. The apparatus and the method have several applications related to assessing olfactory dysfunction of varying severity. The apparatus is of high importance for detecting a person infected with coronavirus (COVID-19), even if he/she is asymptomatic.

The present disclosure relates to olfactory action meter apparatus that is adapted to deliver multiple odors at varying concentrations, from low to high. An odor reservoir contains ten bottles of different odorants and the apparatus is adapted to vary the odorant concentration. The present disclosure provides a method to conduct quantitative olfactory function test to assess loss of olfaction, employing the sensitive olfactory-action meter.

In an aspect, the present disclosure provides an apparatus for quantitative assessment of olfactory dysfunction, the apparatus including one or more first filters configured in the apparatus, the one or more first filter adapted to sterilize air received from an air pump, a second filter coupled to the one or more first filters, the second filter adapted to filter odor molecules from the air, a manifold coupled to the second filter and adapted to split the sterilized air into a plurality of channels, wherein at least one channel of the plurality of channels carries the sterilized air to a first mass flow controller (MFC) and adjacent channels carry sterilized air to one or more second mass flow controllers (MFCs), a reservoir comprising a plurality of containers, each container of the plurality of containers filled with an odorant different from adjacent containers, the sterilized air from each of the one or more second MFCs is received by corresponding containers, wherein predetermined volume of odor vapour discharged from the reservoir mixes with the predetermined volume of sterilized air controlled by the first MFC, the sterilized air from the first MFC is bifurcated into plurality of channels corresponding to containers using solenoid valves, and a nozzle coupled to the reservoir and adapted to receive the odorized air from the reservoir that is inhaled by a subject through an odor delivery unit, the odor delivery unit coupled to the nozzle, wherein based on degree of variation in volumetric concentration of the odorants, quantitative assessment of olfactory dysfunction in the subject is determined.

According to an embodiment, the solenoid valves adapted for precise control over the sterilized air delivery time.

According to an embodiment, the odor delivery unit can be replaceable and adapted to allow the subject to inhale the odorized air, while preventing cross-contamination of the subjects.

According to an embodiment, the odor delivery unit can include suction outlet, wherein the odorized air can be drawn in by a vacuum pump through an electromagnetic valve to provide odor pulses with precise durations.

According to an embodiment, odor delivery unit comprises T-joint and a plurality of common filters, the plurality of common filters placed along length of the T-joint to avoid contamination of the apparatus.

According to an embodiment, the plurality of containers in the reservoir can be filled with pure monomolecular odorant, the odorants are delivered at a varying concentration levels ranging from low to high, wherein the apparatus configured to determine any or a combination of sensory and cognitive aspects of olfaction in the subject.

According to an embodiment, the volumetric concentration of the odorants is a ratio of the volume of odor vapors to the total volume of odorized air, wherein by changing the ratio, different concentration levels ranging from low to high is obtained. According to an embodiment, the vacuum pump coupled to a carbon filter, the exhaust from the vacuum pump is released in the carbon filter.

According to an embodiment, a separating wall configured between the odor delivery unit and associated parts, and the subject to enhance the protection for the subject.

In an aspect, the present disclosure provides a method for quantitative assessment of olfactory dysfunction, the method includes sterilizing, at one or more first filters, air received from an air pump, the one or more first filters configured in the apparatus, removing, at a second filter, odor molecules from the air, the second filter coupled to the one or more first filters, splitting, at a manifold, the sterilized air into a plurality of channels, the manifold coupled to the second filter, wherein at least one channel of the plurality of channels carries the sterilized air to a first mass flow controller (MFC) and adjacent channels carry sterilized air to one or more second mass flow controllers (MFCs), receiving, from each of the one or more second MFCs, sterilized air by corresponding containers in a reservoir, each container of the plurality of containers filled with an odorant different from adjacent containers, wherein predetermined volume of odor vapour discharged from the reservoir mixes with predetermined volume of sterilized air controlled by the first MFC, the sterilized air from the first MFC is bifurcated into plurality of channels corresponding to containers using solenoid valves, and inhaling, by a subject through an odor delivery unit, odorized air received from a nozzle, the nozzle coupled to the reservoir and adapted to receive the odorized air from the reservoir, the odor delivery unit coupled to the nozzle, wherein based on degree of variation in volumetric concentration of the odorants, quantitative assessment of olfactory dysfunction in the subject is determined.

Various objects, features, aspects, and advantages of the inventive subject matter will become more apparent from the following detailed description of preferred embodiments, along with the accompanying drawing figures in which like numerals represent like components.

BRIEF DESCRIPTION OF THE DRAWINGS

The following drawings form part of the present specification and are included to further illustrate aspects of the present disclosure. The disclosure may be better understood by reference to the drawings in combination with the detailed description of the specific embodiments presented herein.

DETAILED DESCRIPTION

The following is a detailed description of embodiments of the disclosure depicted in the accompanying drawings. The embodiments are in such detail as to clearly communicate the disclosure. If the specification states a component or feature "may", "can", "could", or "might" be included or have a characteristic, that particular component or feature is not required to be included or have the characteristic.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The present disclosure relates, in general, to an apparatus for determining olfactory dysfunction, and more specifically, relates to highly sensitive and precise olfactory-action meter apparatus and a method to assess whether a person is suffering from olfactory dysfunction. The apparatus and the method have several applications related to assessing olfactory dysfunction of varying severity. The apparatus is of high importance for detecting person infected with coronavirus (COVID-19), even if he/she is asymptomatic. Moreover, the method identifies severe and persistent olfactory fitness in symptomatic patients during COVID-19 infection. Symptomatic patients showed significant olfactory learning deficits during the infection period in comparison to healthy subjects. On comparing olfactory fitness, differential odor detectabilities and olfactory function scores in symptomatic patients and asymptomatic carriers is found. The present disclosure can be described in enabling detail in the following examples, which may represent more than one embodiment of the present disclosure.

Figure 1A:
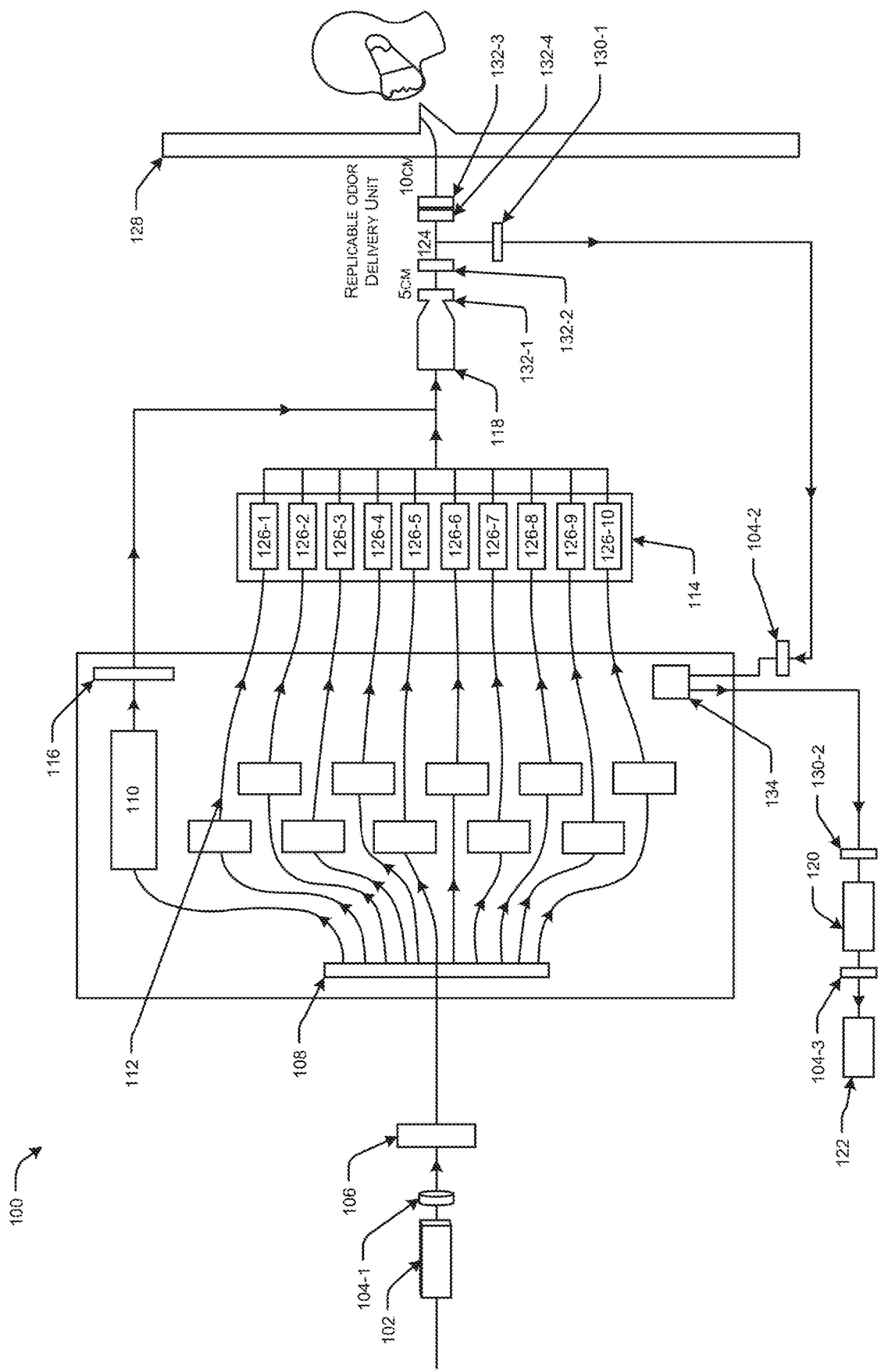
FIG. 1A illustrates an exemplary representation of an olfactory-action meter, in accordance with an embodiment of the present disclosure.

FIG. 1A illustrates an exemplary representation of an olfactory-action meter, in accordance with an embodiment of the present disclosure.

Referring to FIG. 1A, olfactory-action meter 100 (also referred to as an apparatus 100, herein) configured for quantitative assessment of olfactory dysfunction in a subject/patient. The apparatus 100 can include air pump 102, one or more first filters (104-1, 104-2, 104-3), a second filter 106, a manifold 108, a first mass flow controller (MFC) 110 also interchangeably referred to as main mass flow controller (MFC) 110, one or more second mass flow controllers (MFCs) 112 also interchangeably referred to as mini mass flow controllers (MFCs) 112, an odor reservoir 114, one or more solenoid valves 116 (also referred to as solenoid valves 116, herein), a nozzle 118, an odor delivery unit 124, a vacuum pump 120 and a carbon filter 122. The present disclosure conducts precise quantification of olfactory deficits or dysfunction under infectious as well as non-infectious conditions. Further, the present disclosure provides the apparatus 100, which is sensitive, rapid, low-cost, and achieves high-throughput screening of olfactory fitness and cognitive deficits.

In an exemplary embodiment, apparatus 100 as presented in the example may be a ten-channel olfactometer, which can deliver odors with high temporal precision. As can be appreciated, the present disclosure may not be limited to this configuration but may be extended to other configurations. The apparatus 100 delivers odorized air through nozzle 118 into the odor delivery unit 124 through which subjects smell different odors.

In an exemplary embodiment, the one or more first filters (104-1 to 104-3) can be high-efficiency particulate absorbing (HEPA) filters, where the HEPA filters remove harmful particles from the air. In an embodiment, one or more first filters 104-1 can be adapted to sterilize air received from the air pump 102, where the air pump 102 pushes atmospheric air into the apparatus 100 and is subsequently pumped into the second filter 106, the rate of pumping air is 5 liters/min. The second filter 106 coupled to the first filter 104, the second filter 106 adapted to trap/filter the odor molecules from the air. In an exemplary embodiment, the second filter 106 can be an air filter, where the air filter can trap odor molecules from the air and can clean many types of contaminates. The deodorized sterilized air from the second filter 106 can be split into multiple channels by a manifold 108. The manifold 108 coupled to the second filter 106 and can be made of metals.

The manifold 108 coupled to the second filter 106 and adapted split the sterilized air into multiple channels, where at least one channel of the multiple channels carries the sterilized air to the first MFC 110 and adjacent channels carry sterilized air to one or more second MFCs 112. For example, the multiple channels as presented in the example can be eleven channels, where the eleven channels may be connected to ten mini MFCs 112 and one main MFC 110. The operation of the MFCs (110, 112) is software-driven and the experimenter/operator can control the volume of air passing through each of them.

The MFCs may include a microcontroller or other devices capable of being programmed or configured to perform computations and instruction processing in accordance with the disclosure. Such other devices may include microcontrollers, digital signal processors (DSP), complex programmable logic device (CPLD), field programmable gate arrays (FPGA), application-specific assimilated circuits (ASIC), discrete gate logic, and/or other assimilated circuits, hardware or firmware in lieu of or in addition to a microcontroller.

In another embodiment, the odor reservoir 114 (also referred to as reservoir 114, herein) can include one or more containers (126-1 to 126-10 (which are collectively referred to as containers 126, herein)), each container 126 filled with an odorant. In an exemplary embodiment, the odorant can be pure monomolecular odorant. Each container 126 filled with the odorant different from adjacent containers, where the odorants can be delivered at a varying concentration level ranging from low to high, for example, 9% to 50%.

In an exemplary embodiment, reservoir 114 can be made of 15 ml glass bottles/containers 126 with a glass cap with separate channels to receive sterilized/clean air from the second MFCs 112 through an input channel and discharge odorized air through an output channel. Each container 126 can be filled with 4 ml of pure monomolecular odorants. The output from the second MFCs 112 e.g., ten mini MFCs can be coupled to corresponding containers 126 of the reservoir 114. The output from the first MFC 110 can be bifurcated into multiple channels e.g., ten channels corresponding to each container 126 using a battery of solenoid valves 116, where the solenoid valves 116 are provided to obtain precise control over the sterilized/clean air delivery timing.

The predetermined volume of odor vapors discharged from the reservoirs 114 travel through Tygon tubing and mix with a predetermined volume of sterilized/clean air controlled by the main MFC 110 before entering nozzle 118. The nozzle 118 coupled to the reservoir 114 and adapted to receive the odorized air that is inhaled by the subject through the odor delivery unit 124, the odor delivery unit 124 coupled to the nozzle 118 adapted to allow the subject to inhale the odorized air, while preventing cross-contamination of the subjects. The odorized air is first drawn in by the vacuum pump 120 through an electromagnetic valve 134. This helps in making odor pulses with precise durations. The suction outlet placed outside the exit of the nozzle 118 diverts air through a series of three 0.2 mm filters that can include HEPA filters (104-2, 104-3) and Polyethersulfone (PES) filters 130-1 into the exhaust activated carbon filter 122. The output towards the vacuum pump 120 can be guarded by 0.2 mm PES filter 130-2.

The vacuum pump 120 is operating at a capacity of ~450 millibar (mbar). The exhaust from the vacuum pump 120 can be released in the carbon filter 122, which can be coupled to the vacuum pump 120. The vacuum is always functional except during the odor delivery, during which air travels from the odor nozzle to the tip of the odor delivery unit 124. The odor delivery unit 124 can include T-joint, common filters (132-1 to 132-4) and PES filters (130-1). The apparatus 100 is protected from any contaminants getting inside with series of filters and high vacuum. Further, cross-contamination is prevented by using sterilized odor delivery unit 124 for each patient/subject.

In an exemplary embodiment, the T-joint is 15 cm in length and can be replaceable, the T-joint can be sterilised before each use to avoid cross-contamination between the subjects. The T-joint can include four different layers of common filters (132-1 to 132-4 which are collectively referred to as common filters 132, herein) made from surgical mask grade material, the common filters 132 can be placed along the length of the T-joint to avoid instrument contamination. In another embodiment, the PES filters of the odor delivery unit 124 can be coupled to the vacuum pump 120 operating at 450 mbar. The exhaust line can be additionally fitted with two 0.2 mm HEPA filters (104-2, 104-3) and one 0.2 mm PES filter 130-2 before the exhaust can be released to a 60 cm long activated carbon filter 122.

In another embodiment, based on degree of variation in volumetric concentration of the odorants, quantitative assessment of olfactory dysfunction and neurocognitive deficits in the subject can be determined. The apparatus 100 configured to determine any or a combination of sensory and cognitive aspects of olfaction in the subject. The total odorized airflow/air is thus the sum of the volume of odor vapors and the volume of sterilized air/clean air. The volumetric concentration (% v/v) of the odor can therefore be defined as the ratio of the volume of odor vapors to the total volume of odorized air. By changing the ratio, different concentrations may be achieved for each of the odors used. The detection threshold can be measured separately for each odor and the detection accuracy can be calculated for each concentration level. Odor duration and inter-trial interval can be varied as per the needs of odor detection measurements. Further, a separating wall 128 can be configured between the odor delivery unit 124 and the subject to enhance the protection for the subject.

Figure 1B:
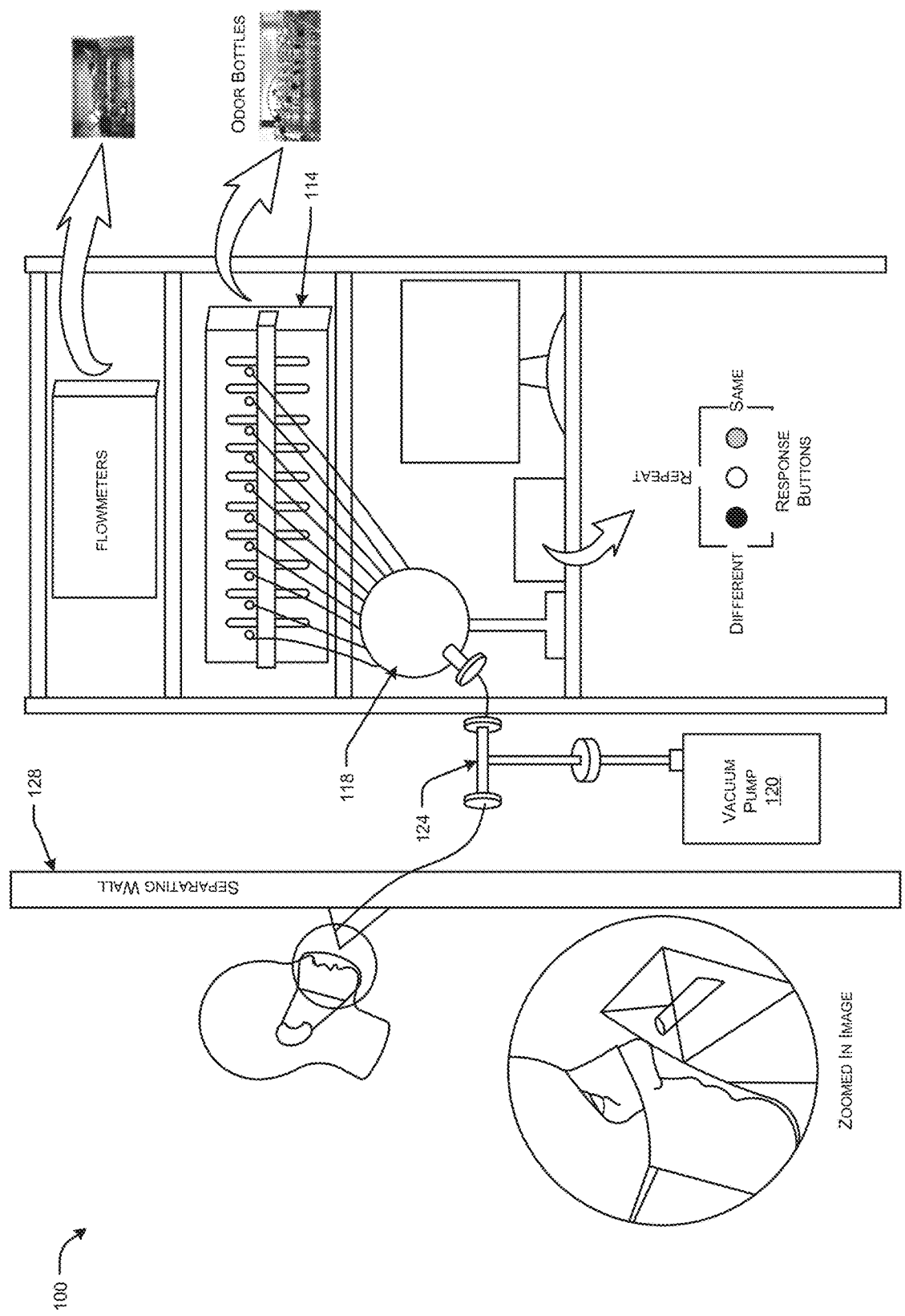
FIG. 1B illustrates a schematic view of olfactory-action meter, in accordance with an embodiment of the present disclosure.

The embodiments of the present disclosure described above provide several advantages. The one or more of the embodiments discloses the olfactory-action meter 100 which is sensitive, rapid, low-cost, and achieves high-throughput screening of olfactory fitness and cognitive deficits. The apparatus 100 provides separate optimized paradigms to pick up sensory and cognitive deficits and enables real-time update of the performance. The apparatus 100 provides a readout of mass flow controllers, which allows the operator to monitor the flow rates in real-time and modify if needed. The present disclosure provides the advantage of getting verbal readouts from patients with infectious diseases and recording a motor action by pressing the button as shown in FIG. 1B of a response box in case of non-infectious diseases e.g., Parkinson's Disease. The buttons can be coupled to computing device. The present disclosure provides a layout of the response box, where use of repeat button if the subjects are not able to sample either of the odors in odor matching paradigm.

The present disclosure can customize the paradigm to the needs of clinical requirements to probe different olfactory abilities. The variable parameters are a duration of odor pulse, inter-stimulus interval and inter-trial interval. Depending on the needs, a screen can be placed in front of the subject, which can give a visual indication of the delivery of odors and response timers. This allows to record the reaction times shown by subjects, which is crucial for patients with Parkinson's disease.

Figure 2A:
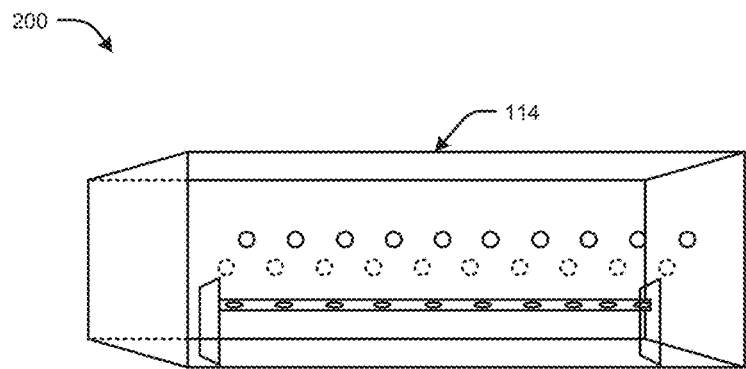
FIG. 2A illustrates an exemplary view of reservoir, in accordance with an embodiment of the present disclosure.
Figure 2A:
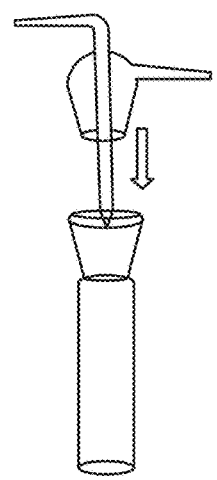

FIG. 2A illustrates an exemplary view of reservoir, in accordance with an embodiment of the present disclosure.

Referring to FIG. 2A, the odor reservoir 114 can include one or more containers 126, each container 126 adapted to be filled with an odorant different from adjacent containers. The reservoir 114 can be made of 15 ml glass bottles/containers with a glass cap with separate channels to receive sterilized/clean air from the second MFCs 112 through the input channel and discharge odorized air through the output channel as shown in FIG. 2A.

Figure 2B:
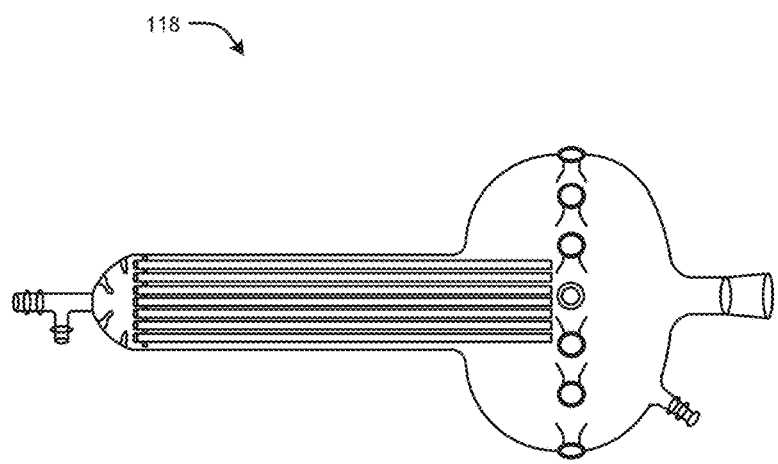
FIG. 2B illustrates an exemplary view of nozzle, in accordance with an embodiment of the present disclosure.
Figure 2B:
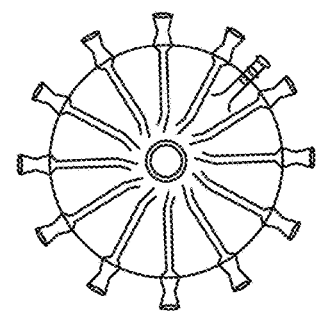

FIG. 2B illustrates an exemplary view of nozzle, in accordance with an embodiment of the present disclosure. The odor vapors from the reservoirs 114 travel through Tygon tubing and mixes with a stream of sterilized/clean air controlled by the main MFC 110 before entering the nozzle 118. The nozzle 118 coupled to the reservoir 114 and adapted to receive the odorized air from the reservoir 114 that is inhaled by the subject through the odor delivery unit 124, the odor delivery unit 124 coupled to the nozzle 118. The nozzle can be made of glass.

The suction outlet placed outside the exit of the nozzle 118 diverts air through a series of three 0.2 mm filters that can include HEPA filters (104-2, 104-3) and Polyethersulfone (PES) filters 130-1 into the exhaust activated carbon filter 122. The output towards the vacuum pump 120 can be guarded by 0.2 mm PES filter 130-2.

The present disclosure requires minimum training to operate the apparatus 100 and can be handled easily. The apparatus 100 can use different types of odors which can be extrapolated to identification task if socially relevant odors are used. The apparatus 100 delivers each odor using a separate channel, hence mixing of the odors can be prevented. Further, the apparatus 100 enables independent control of the mass flow controllers that allows odors to be delivered in different combinations. As ten independent odor lines are present, many mixtures of varying complexity can be generated.

Figure 3A:
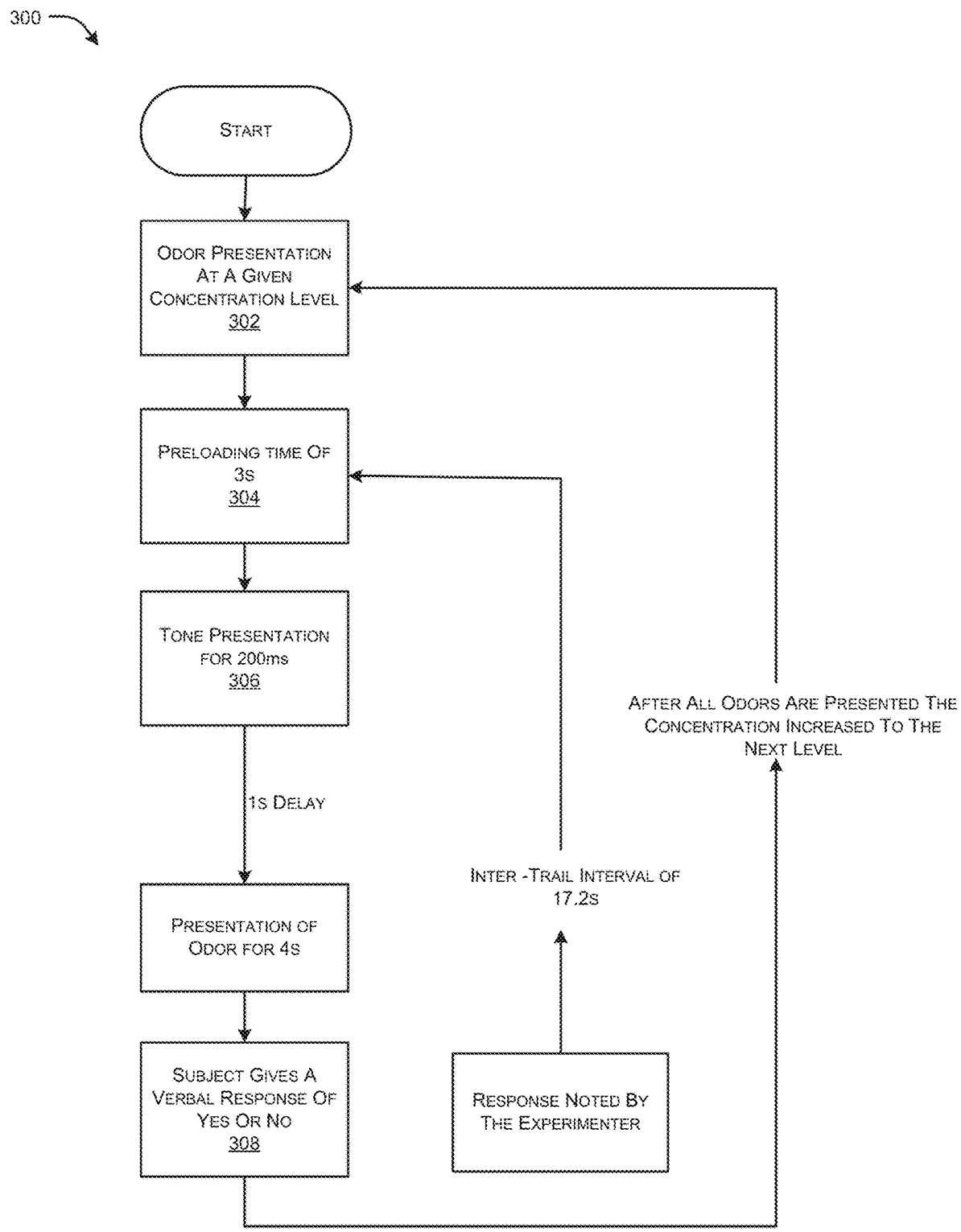
FIG. 3A illustrates an exemplary method for measuring odor detection indices of stimuli with varying physico-chemical properties, in accordance with an embodiment of the present disclosure.

FIG. 3A illustrates an exemplary method 300 for measuring odor detection indices of stimuli with varying physico-chemical properties, in accordance with an embodiment of the present disclosure.

Referring to FIG. 3A, odor detection measurements include ten different odorants that can be delivered at different concentrations. The method includes at block 302 a specific odor concentration is determined by an experimentalist/operator to deliver it to the subject/individual/patient. At block 304, a preloading time is set during which the odorized air travelled through the nozzle 118 into the odor delivery unit 124. The odorized air can be diverted into the suction line of the odor delivery unit 124. The preloading time ensured a sharp odor pulse and minimized the delay in odor delivery.

At block 306, after the preloading time elapsed, the odorized air travelled to the tip of the odor delivery unit 124 into the nasal cavity of the participant/subject, the tone presentation of 200 ms is initiated prior to the odor delivery.

At block 308, at the end of the odor delivery, the subject gives a verbal response of 'YES' or 'NO' depending on whether they detected the odor or not. In this manner, all the odors are presented to the individual. After all the odors are presented, these steps are repeated for every odor concentration.

All odors were sequentially delivered at a particular concentration level and then the concentration can be increased to the next level. It may be noted that the time duration shown in the figures are for illustrative purpose only and do not restrict the method to the timings.

Figure 3B:
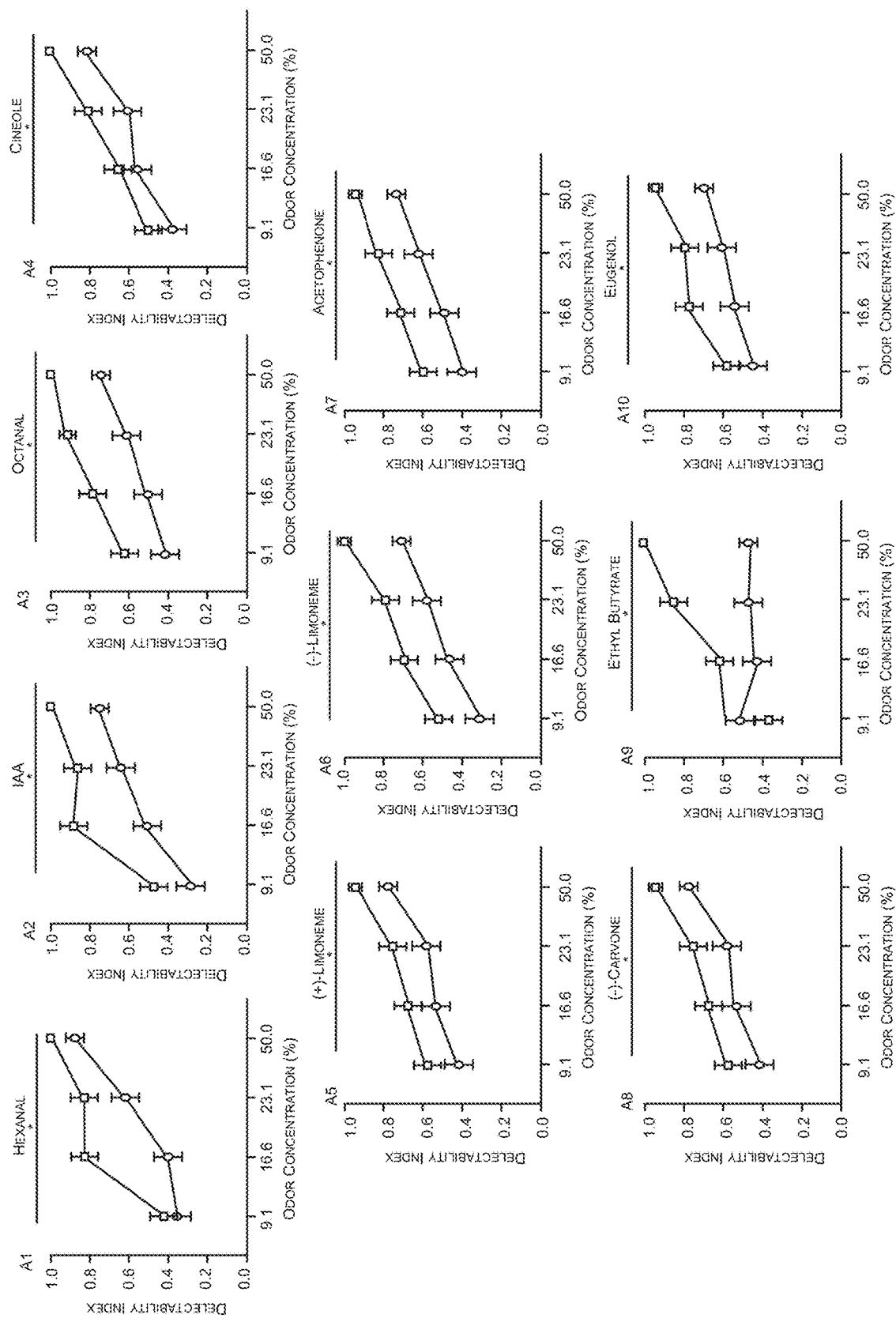
FIG. 3B illustrates a graphical view of odor detectabilities of symptomatic COVID-19 patients and normal healthy subjects, in accordance with an embodiment of the present disclosure.

FIG. 3B illustrates a graphical view of odor detectabilities of symptomatic COVID-19 patients and normal healthy subjects, in accordance with an embodiment of the present disclosure.

An experiment conducted from laboratory has reported significant olfactory deficits in asymptomatic COVID-19 patients. This was inferred after analyzing both olfactory detection and matching skills. A total of 6591 behavioural readouts from 121 subjects (71 males and 50 females) participated in olfactory fitness test using the custom-built olfactory action-meter 100. A) Ten monomolecular odors, each at four different odor concentrations, are used for the detection task. Firstly, the olfactory detectability indices (DI) at four different concentrations increasing from 9.1% (v/v) to 50% (v/v) for a total of 10 odors is measured. Every odor at a given concentration is delivered for 4 s using the custom-built olfactometer. Participants verbally confirm successful detection. Four of the successfully detected odors at 50% concentrations are further used for olfactory matching experiment.

B) odor-wise detection indices show a significant deficiency in COVID-19 patients (N=49) in comparison to healthy subjects (N=52). Two-way analysis of variance (ANOVA) with Bonferroni's multiple comparison test, $*p<0.05$, $p<0.01$, $*p<0.001$, $****p<0.0001$. The overall DI index for all the odors used for detection task shows that symptomatic COVID-19 patients (N=49, 2699 readouts) had poor mean DI for a total of 10 odors, of 0.49 at 16.6% (v/v), 0.59 at 23.1% (v/v) and 0.73 at 50% (v/v) as compared to healthy subjects (N=52, 3092 readouts)

C) Detectability index plotted for different odor concentration for control/healthy subjects (N=52) and patients (N=49) groups (Two-way ANOVA with Bonferroni's multiple comparison, 0.72, 0.82 and 0.97 respectively, p=0.0011 for 16.6%, p=0.0014 for 23.1% and p<0.0001 for 50% concentration, respectively).

D) Receiver operating characteristic (ROC) analysis for predicting olfactory impairment using DI measured for different concentrations of different odors in COVID-19 patients. ROC analysis shows an accuracy (AUC) of 0.88, specificity (SP) of 0.80, sensitivity (SE) of 0.86, positive predictive value (PPV) of 0.7959, negative predictive value (NPV) of 0.87 for prediction based on DI measured from healthy subjects (N=52) and COVID-19 patients (N=45). Values shown in the figure with 95% confidence interval is indicated in grey.

Figure 4A:
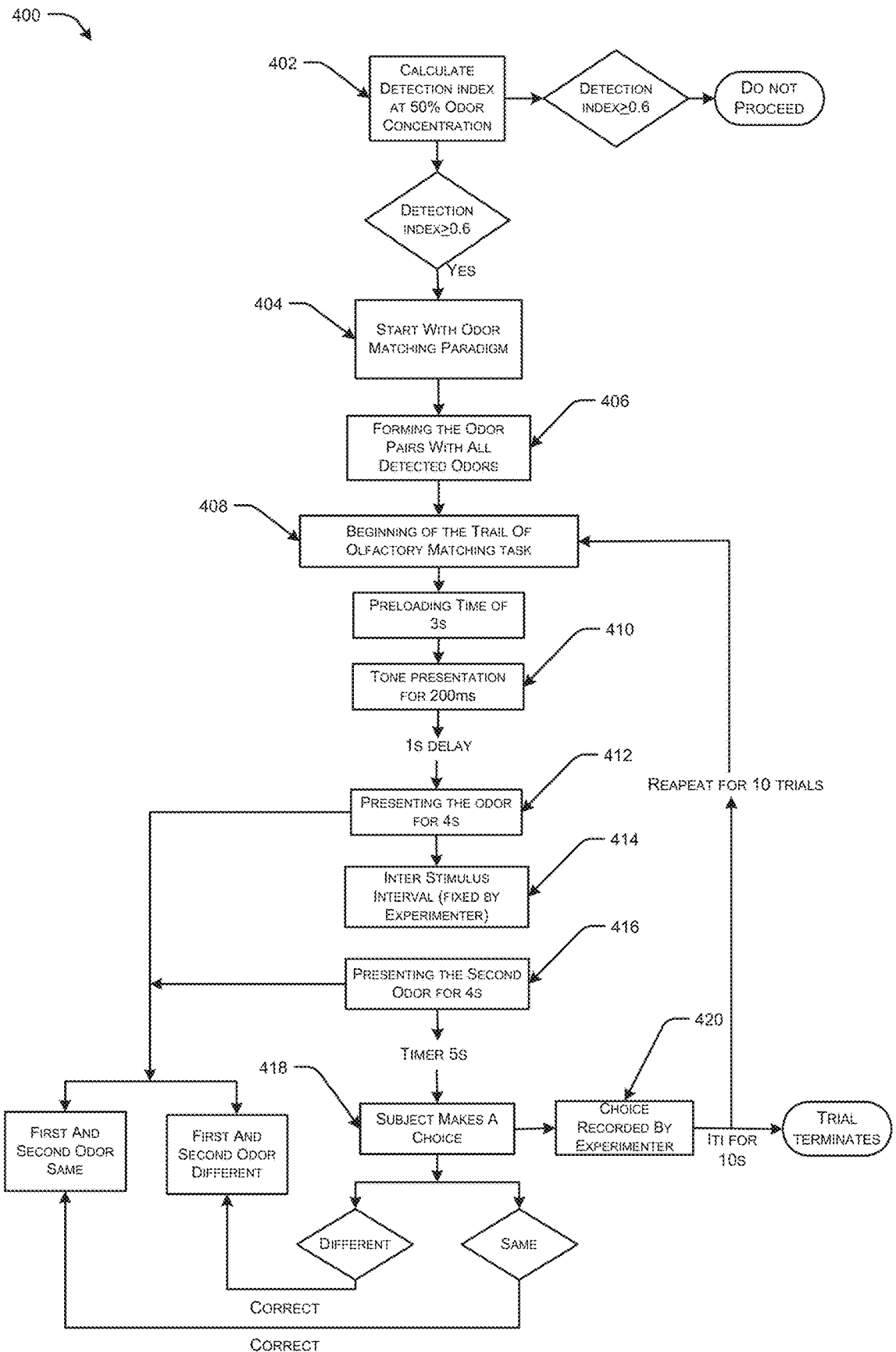
FIG. 4A illustrates an exemplary method for measuring odor matching performance indices, in accordance with an embodiment of the present disclosure.

FIG. 4A illustrates an exemplary method for measuring odor matching performance indices 400, in accordance with an embodiment of the present disclosure.

Referring to FIG. 4A, the method includes at block 402, calculate detection index at 50% odor concentration. At block 404, determine odor matching paradigm with detection index greater than equal to 0.6 at 50% concentration to initiate odor matching paradigm. At block 406, the odor pairs with all detected odor is formed. At block 408, the trial of the olfactory matching task is performed, each session consisted of ten trials. At block 410, the trial is initiated with a tone presentation for 200 ms.

At block 412, after is delay, a first odor can be delivered, the odor can be delivered for 4 s and then, at block 414, an inter-stimulus interval of 5 s may be fixed by the operator after which at block 416, the second odor can be delivered for 4 s. At block 418, the two odors presented can either be the same or different and the subjects were expected to compare the two odors delivered sequentially and assess if the odors were 'SAME' or 'DIFFERENT'. At block 420, the subjects are expected to give a verbal response after the second odor delivery, where the response can be registered using a response console by the operator.

The present disclosure has applications in which there is a necessity for determining whether the person is suffering olfactory dysfunction. However, the disclosure is extremely useful in determining whether the person is COVID-19 positive, even if he/she is asymptomatic.

Readouts from the olfactory-action meter can be indicative of olfactory sensory as well as cognitive deficits caused by infection. Therefore, this method can efficiently be used to screen and reliably find subjects with infectious diseases, which do not show any symptoms of infection and can be termed as asymptomatic carriers of the disease.

Figure 4B:
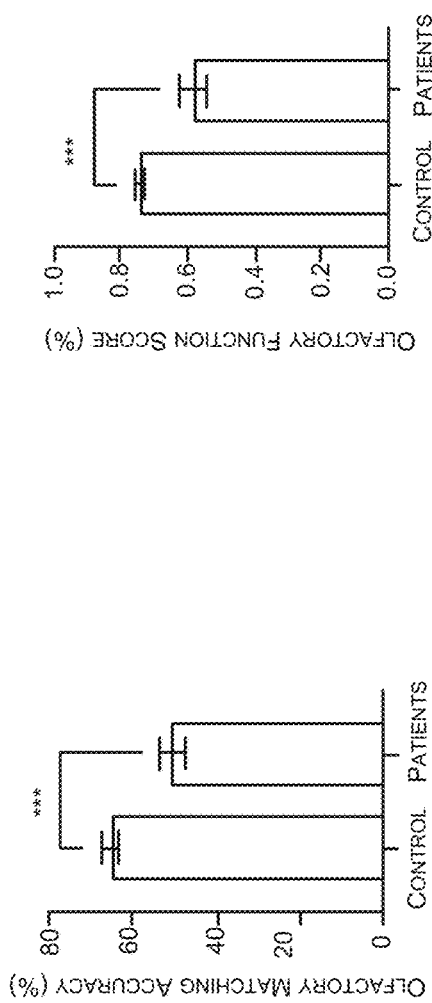
FIG. 4B illustrates an exemplary graphical view of olfactory fitness and learning abilities measured in COVID-19 patients, in accordance with an embodiment of the present disclosure.
Figure 4B:
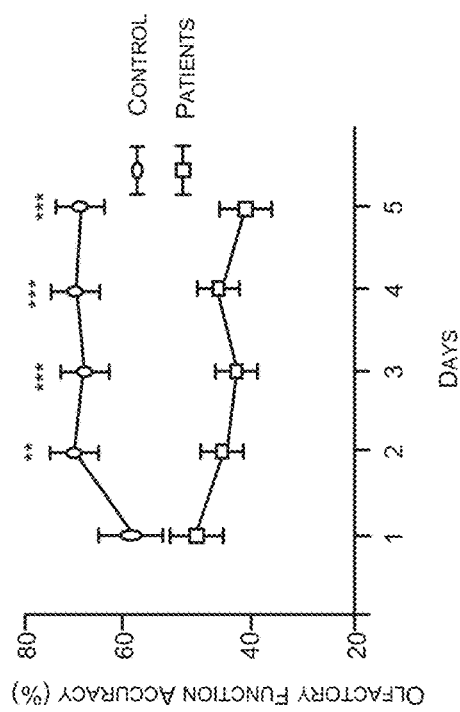
Figure 4B:
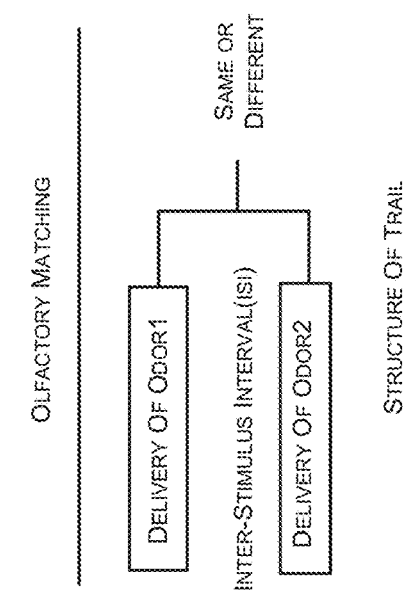
Figure 4B:
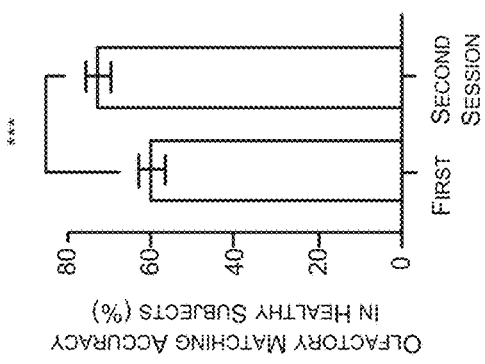

FIG. 4B illustrates an exemplary graphical view of olfactory fitness and learning abilities measured in COVID-19 patients, in accordance with an embodiment of the present disclosure.

The olfactory matching abilities of patients and normal healthy subjects with >0.6 DI scores at 50% concentration are investigated. Olfactory matching accuracy reflects their discrimination efficiency as well as working memory. Therefore, it can be used as an efficient readout for cognitive deficits.

A) Each trial comprises of two odors being delivered, each for 4 s, separated by an inter-stimulus interval (ISI) of 5 s. Verbal response of the subject is recorded on whether the two odors are same or different. Odor matching accuracy for each session is calculated based on the number of correct responses at the end of each session.

B) Olfactory matching accuracy plotted for patients (N=40) and control (N=52) subjects. Matching accuracy calculated based on the number of correct responses after 10 trials. Patients with low DIs (N=9) did not perform odor matching, thus excluded from this analysis. When measured the odor matching accuracy for control/healthy subjects (N=52) and patient (N=40) groups, patients had significantly lower mean olfactory matching accuracy compared to the control subjects.

C) Olfactory function score (OFS) of the control (N=52) and patients (N=48) have been plotted. The olfactory function score is calculated by providing equal weightage to odor detection values at 4 different concentrations and the olfactory matching accuracy. It is found that significantly lower olfactory function score in symptomatic COVID-19 patients (olfactory function score average value=0.743 for controls (N=52), and 0.5853 for patients (N=48), Unpaired two-tailed t-test, *** p=0.0004].

D) For further probing if their olfactory matching skills can be improved over time, the olfactory matching test is performed for 4 or more consecutive days during their active infection period. For this continuous testing, 4 odorants for which the DIs were comparable at 50% (v/v) is utilized between the patients and healthy subjects (p>0.05, Unpaired t-test). A pilot study from the laboratory had shown improved matching accuracies (72.75% average olfactory matching in session 2 as compared to 60% in session 1) for pairs of 10 monomolecular odorants during the second session of testing. The olfactory matching accuracies plotted for healthy subjects (N=20) for two consecutive sessions. Matching accuracy calculated based on the number of correct responses after 20 trials. (Paired two-tailed t-test,*** p=0.0008).

E) To check if olfactory perceptual learning and memory is affected in the patients suffering from COVID-19, the olfactory matching test is carried out for minimum 4 days with the patients who agreed to participate (a total of 1090 readouts from N=12 for both patient and healthy subject groups). Healthy subjects who started at an average accuracy of 60.83% on day 1 of the task consistently improved over days reaching 70% on day 5. COVID-19 patients, on the other hand, had an average accuracy fluctuating between 40% to 48.75% across all testing days, which evidently indicated learning deficits in COVID-19 patients. Matching accuracies calculated based on the number of correct responses after 10 trials in each session. (Two-way ANOVA with Bonferroni's multiple comparison, p=0.68 for day 1, p=0.0011 for day 2, * p=0.0005 for day 3, p=0.0008 for day 4 and p=0.0007 for day 5).

The proposed apparatus 100 provides benefits such as quantitatively detecting sensory and cognitive deficits with high precision and accuracy with subjects with or without infection of a disease such as Covid-19. The apparatus of the present disclosure also comes with the provision to generate many stimuli of varying complexity by using multiple odors. The accuracy of detection is more than 80%. Cross-contamination between tested patients/subjects is prevented by replaceable stimulus delivery units and the separating wall between the apparatus 100 and test subject. Further, as each odor is delivered using separate channel, there is no mixing of the odors.

In the tests/experiments conducted to determine the accuracy of the apparatus for the COVID-19 situation, it was found that asymptomatic COVID-19 persons displayed significantly reduced odor detection capabilities compared to the normal healthy individuals, particularly at lower concentration levels. Comparison of detection scores shown by patients and normal healthy subjects showed that up to 81% of the asymptomatic patients had olfactory dysfunctions and failed in detecting odorants at low concentrations.

Figure 5:
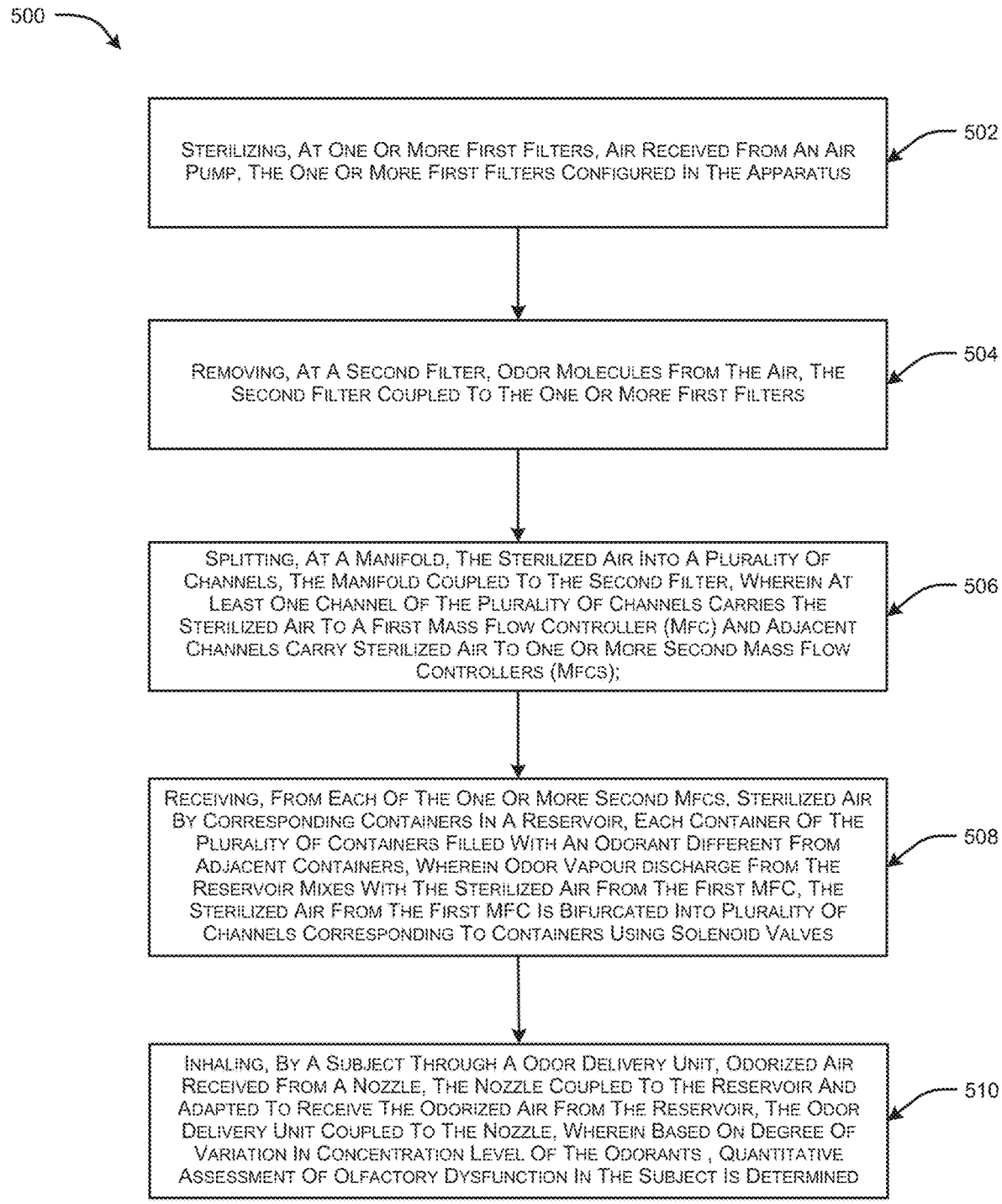
FIG. 5 illustrates an exemplary method for quantitative assessment of olfactory dysfunction, in accordance with an embodiment of the present disclosure.

FIG. 5 illustrates an exemplary method for quantitative assessment of olfactory dysfunction, in accordance with an embodiment of the present disclosure.

Referring to FIG. 5, the method includes at block 502 one or more first filters can sterilize air received from an air pump, the one or more first filters configured in the apparatus. At block 504 second filter can remove odor molecules from the air, the second filter coupled to the one or more first filters. At block 506, manifold can split the sterilized air into a plurality of channels, the manifold coupled to the second filter, where at least one channel of the plurality of channels carries the sterilized air to a first MFC and adjacent channels carry sterilized air to one or more second MFCs.

At block 508, each container of the plurality of containers filled with an odorant different from adjacent containers, the sterilized air from each of the one or more second MFCs is received by corresponding containers, where predetermined volume of odor vapour discharged from the reservoir mixes with predetermined volume of sterilized air controlled by the first MFC, the sterilized air from the first MFC is bifurcated into plurality of channels corresponding to containers using solenoid valves.

At block 510, a nozzle coupled to the reservoir and adapted to receive the odorized air from the reservoir that is inhaled by a subject through an odor delivery unit, the odor delivery unit coupled to the nozzle, wherein based on degree of variation in volumetric concentration of the odorants, quantitative assessment of olfactory dysfunction in the subject is determined.

The present disclosure provides apparatus 100, the custom-built olfactory-action meter that measures olfactory fitness with high precision, but with built-in safety precautions to prevent cross-contamination. Using the olfactory-action meter, olfactory dysfunction in 82% of asymptomatic COVID-19 carriers is identified, which is remarkable, because only 15% of the subjects reported a loss of olfaction in self-reporting paradigms. The proposed method therefore lays the foundation for an olfaction-based test that could identify asymptomatic carriers with high sensitivity and thereby help to prevent the rampant spread of COVID-19. The present disclosure provides novel screening method that analyzes both detection indices at varying odor concentrations as well as olfactory matching abilities across various odors. This method can therefore detect both sensory and cognitive aspects of olfaction. Optimization of experimental parameters by testing normal healthy subjects enabled us to screen a single patient in less than 20 minutes without compromising accuracy. The olfactory-action meter can highly reliably identify asymptomatic carriers.

The present disclosure enables to quantify the olfactory fitness from symptomatic COVID-19 patients using our custom-built olfactory action meter. On analyzing a total of 6591 readouts from 121 subjects (including patients and normal healthy subjects), it is observed significantly reduced detectability indices and olfactory matching accuracies for symptomatic COVID-19 patients compared to normal healthy subjects for all concentrations tested using 10 different odorants of varying physico-chemical properties. The present disclosure selects subset of subjects from the above-mentioned readouts who qualified for their detectabilities and continued assessing their learning abilities using olfactory matching test over days. The results show significantly reduced learning abilities for COVID-19 patients compared to normal healthy subjects. Finally, on comparing olfactory detectabilities and neurocognitive readouts, significant differences between symptomatic COVID-19 patients and asymptomatic carriers is determined. The obtained results therefore substantiate the necessity for long-term tracking via quantification of neurocognitive deficits/frailties during post-infection period.

It will be apparent to those skilled in the art that the apparatus 100 of the disclosure may be provided using some or all of the mentioned features and components without departing from the scope of the present disclosure. While various embodiments of the present disclosure have been illustrated and described herein, it will be clear that the disclosure is not limited to these embodiments only. Numerous modifications, changes, variations, substitutions, and equivalents will be apparent to those skilled in the art, without departing from the scope of the disclosure, as described in the claims.

Advantages of the Present Disclosure

The present disclosure provides an apparatus which is sensitive, rapid, low-cost, and achieves high-throughput screening of olfactory fitness and cognitive deficits.

The present disclosure provides an apparatus that provides separate optimized paradigms to pick up sensory and cognitive deficits.

The present disclosure provides an apparatus that enables real-time update of the performance.

The present disclosure provides an apparatus that provides a readout of mass flow controllers, which allows the operator to monitor the flow rates in real-time and modify if needed.

The present disclosure requires minimum training to operate the apparatus and can be handled easily.

The present disclosure provides the use of different types of odors, which can be extrapolated to identification task if socially relevant odors are used.

The present disclosure provides an apparatus that delivers each odor using a separate channel, hence mixing of the odors can be prevented.

The present disclosure provides an apparatus that enables independent control of the mass flow controllers that allows odors to be delivered in different combinations. As ten independent odor lines are present, many mixtures of varying complexity can be generated.

The present disclosure provides the advantage of getting verbal readouts from patients with infectious diseases and recording a motor action by pressing the button of a response box in case of non-infectious diseases.

The present disclosure provides a layout of the response box, where use of repeat button if the subjects are not able to sample either of the odors in odor matching paradigm.

The present disclosure can customize the paradigm to the needs of clinical requirements to probe different olfactory disabilities. The variable parameters are duration of odor pulse, inter-stimulus interval and inter-trial interval. This allows to get the readout of working memory.

The present disclosure provides an apparatus in which depending on the needs, a screen can be placed in front of the subject, which can give a visual indication of the delivery of odors and response timers. This allow to record the reaction times shown by subjects, which is crucial for patients with Parkinson's Disease.

I claim:

1. An apparatus (100) for quantitative assessment of olfactory dysfunctions and cognitive deficits, the apparatus comprising:
    one or more first filters (104-1) configured in the apparatus, the one or more first filters adapted to sterilize air received from an air pump (102);
    a second filter (106) coupled to the one or more first filters, the second filter adapted to filter odor molecules from the air;
    a manifold (108) coupled to the second filter (106) and adapted to split the sterilized air into a plurality of channels, wherein at least one channel of the plurality of channels carries the sterilized air to a first mass flow controller (MFC) (110) and adjacent channels carry sterilized air to one or more second mass flow controllers (MFCs) (112);
    a reservoir (114) comprising a plurality of containers (126), each container of the plurality of containers filled with an odorant different from adjacent containers, the sterilized air from each of the one or more second MFCs (112) is received by corresponding containers (126),
    wherein the plurality of containers (126) in the reservoir (114) is filled with pure monomolecular odorant, the odorants are provided at a varying concentration level ranging from low to high,
    wherein predetermined volume of odor vapour discharged from the reservoir (114) mixes with predetermined volume of sterilized air controlled by the first MFC (110), the sterilized air from the first MFC (110) is bifurcated into a plurality of channels corresponding to containers using solenoid valves (116); and a nozzle (118) coupled to the reservoir (114) and adapted to receive the odorized air from the reservoir (114) that is inhaled by a subject through an odor delivery unit (124), the odor delivery unit coupled to the nozzle, wherein based on degree of variation in volumetric concentration of the odorants, quantitative assessment of olfactory dysfunction in the subject is determined; wherein the volumetric concentration of the odorants is a ratio of the volume of odor vapors to the total volume of odorized air, wherein by changing the radio, different concentration levels ranging from low to high are obtained;

wherein the odor delivery unit (124) comprises a suction outlet, a T-joint and a plurality of common filters (132-1 to 132-4).

2. The apparatus as claimed in claim 1, wherein the solenoid valves (116) are adapted for precise control over the sterilized air delivery time.

3. The apparatus as claimed in claim 1, wherein the odor delivery unit (124) is replaceable and adapted to allow the subject to inhale the odorized air, while preventing cross-contamination among different subjects.

4. The apparatus as claimed in claim 3, wherein the odorized air is drawn in by a vacuum pump (120) through an electromagnetic valve (134) to provide odor pulses with precise durations.

5. The apparatus as claimed in claim 4, wherein the vacuum pump (120) is coupled to a carbon filter (122), and exhaust from the vacuum pump is released in the carbon filter (122).

6. The apparatus as claimed in claim 1, wherein the plurality of common filters (132-1 to 132-4) are placed along length of the T-joint to avoid contamination of the apparatus.

7. The apparatus as claimed in claim 1, wherein the apparatus is configured to determine any or a combination of sensory and cognitive aspects of olfaction in the subject.

8. The apparatus as claimed in claim 1, wherein a separating wall (128) is configured between the odor delivery unit (124) and the subject to enhance protection for the subject.

9. A method (500) for quantitative assessment of olfactory dysfunctions and cognitive deficits, the method comprising:

sterilizing (502), at one or more first filters, air received from an air pump, the one or more first filters configured in the apparatus;

removing (504), at a second filter, odor molecules from the air, the second filter coupled to the one or more first filters;

splitting (506), at a manifold, the sterilized air into a plurality of channels, the manifold coupled to the second filter, wherein at least one channel of the plurality of channels carries the sterilized air to a first mass flow controller (MFC) and adjacent channels carry sterilized air to one or more second mass flow controllers (MFCs);

receiving (508), from each of the one or more second MFCs, sterilized air by corresponding containers in a reservoir, each container of the plurality of containers filled with an odorant different from adjacent containers, wherein predetermined volume of odor vapour discharged from the reservoir mixes with predetermined volume of sterilized air controlled by the first MFC, the sterilized air from the first MFC is bifurcated into a plurality of channels corresponding to containers using solenoid valves; and inhaling (510), by a subject through an odor delivery unit, odorized air received from a nozzle, the nozzle coupled to the reservoir and adapted to receive the odorized air from the reservoir, the odor delivery unit coupled to the nozzle, wherein based on degree of variation in volumetric concentration of the odorants, quantitative assessment of olfactory dysfunction in the subject is determined.

* * * * *